(12) United States Patent
Abad (10) Patent No.: US 9,579,308 B2
(45) Date of Patent: *Feb. 28, 2017

(54) COMPOSITIONS AND METHODS FOR TREATING PRESBYOPIA, MILD HYPEROPIA, AND IRREGULAR ASTIGMATISM

(71) Applicant: ALLERGAN, INC., Irvine, CA (US)

(72) Inventor: Juan Carlos Abad, Medellin, CO (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/129,012

(22) PCT Filed: Sep. 19, 2012

(86) PCT No.: PCT/IB2012/002335
§ 371 (c)(1),
(2) Date: Dec. 23, 2013

(87) PCT Pub. No.: WO2013/041967
PCT Pub. Date: Mar. 28, 2013

(65) Prior Publication Data
US 2014/0200211 A1    Jul. 17, 2014

Related U.S. Application Data

(60) Provisional application No. 61/536,921, filed on Sep. 20, 2011.

(51) Int. Cl.
| | |
|---|---|
| *A61K 31/4174* | (2006.01) |
| *A61K 31/4178* | (2006.01) |
| *A61K 45/06* | (2006.01) |
| *A61K 9/00* | (2006.01) |
| *A61K 31/27* | (2006.01) |
| *A61K 31/4164* | (2006.01) |
| *A61K 31/5415* | (2006.01) |
| *A61K 31/16* | (2006.01) |
| *A61K 31/325* | (2006.01) |

(52) U.S. Cl.
CPC ........ *A61K 31/4178* (2013.01); *A61K 9/0048* (2013.01); *A61K 31/16* (2013.01); *A61K 31/27* (2013.01); *A61K 31/325* (2013.01); *A61K 31/4164* (2013.01); *A61K 31/4174* (2013.01); *A61K 31/5415* (2013.01); *A61K 45/06* (2013.01)

(58) Field of Classification Search
CPC ............ A61K 31/4174; A61K 31/4178; A61K 31/4164
See application file for complete search history.

(56) References Cited

U.S. PATENT DOCUMENTS

| | | |
|---|---|---|
| 3,670,087 A | 6/1972 | Lorenzetti |
| 5,055,467 A | 10/1991 | Albaugh |
| 5,122,522 A | 6/1992 | Laties et al. |
| 5,422,116 A | 6/1995 | Yen et al. |
| 5,459,133 A | 10/1995 | Neufeld |
| 5,488,050 A | 1/1996 | Neufeld |
| 5,767,143 A | 6/1998 | Lehmussaari et al. |
| 5,776,916 A | 7/1998 | Gramer |
| 6,066,675 A | 5/2000 | Wen et al. |
| 6,164,282 A | 12/2000 | Gwon et al. |
| 6,273,092 B1 | 8/2001 | Nolan |
| 6,291,466 B1 | 9/2001 | Gwon et al. |
| 6,291,498 B1 | 9/2001 | Horn |
| 6,410,544 B1 | 6/2002 | Gwon et al. |
| 6,420,407 B1 | 7/2002 | Horn |
| 6,495,603 B1 | 12/2002 | Miyake et al. |
| 6,515,006 B2 | 2/2003 | Horn |
| 6,730,065 B1 | 5/2004 | Horn |
| 6,730,691 B1 | 5/2004 | Galin |
| 7,105,512 B2 | 9/2006 | Morizono et al. |
| 8,299,079 B2 | 10/2012 | Kaufman |
| 8,475,831 B2 | 7/2013 | Sancho |
| 8,524,758 B2 | 9/2013 | Benozzi |

(Continued)

FOREIGN PATENT DOCUMENTS

| | | |
|---|---|---|
| AR | 08104 | 6/2012 |
| EP | 11004801 B1 | 9/2003 |

(Continued)

OTHER PUBLICATIONS

Vaidyanathan et al., Fluticasone Reverses Oxymetazoline-inducedTachyphylaxis of Response and Rebound Congestion, American Journal of Respiratory and Critical Care Medicine, vol. 182, 2010, pp. 19-24.
Akers, M.J., Antioxidants in Pharmaceutical Products, Journal of Parenteral Science and Technology, vol. 36 No. 5, 1982, pp. 222-228.
Beck-Speier et al., Oxymetazoline Inhibits Proinflammatory Reactions: Effect on Arachidonic Acid-Derived Metabolites, The Journal of Pharmacology and Experimental Therapeutics, vol. 316, No. 2, 2006, pp. 843-851.
Chu, T. C. et al., Oxymetazoline: Potential Mechanisms of Inhibitory Effects on Aqueous Humor Dynamics, Pharmacology, Department of Pharmacology and Toxicology, Morehouse School of Medicine, vol. 53, 1996, pp. 259-270.
Congdon et al., Corneal complications associated with topical ophthalmic use of nonsteroidal anti-inflammatory drugs, J. Cataract Refract Surg., vol. 27, Apr. 2001, pp. 622-631.
Duzman et al., Topically Applied Oxymetazoline, Ocular Vasoconstrictive Activity, Pharmacokinetics, and Metabolism, Arch. Ophthalmol., vol. 101, 1983, pp. 122-1126.

(Continued)

*Primary Examiner* — Zohreh Fay
(74) *Attorney, Agent, or Firm* — Lorenz Siddiqi (57) ABSTRACT

The present invention is directed to compositions and methods for treating presbyopia, mild hyperopia, and irregular astigmatism. The compositions include a cholinergic agent, such as a muscarinic acetylcholine receptor $M_3$ agonist, and an alpha agonist having an imidazoline group or a non-steroidal anti-inflammatory agent (NSAID) having COX-2 selectivity. It has been found that an alpha agonist having an imidazoline group or non-steroidal anti-inflammatory agent (NSAID) having COX-2 selectivity in combination with a cholinergic agent, such as pilocarpine, act synergistically to improve the accommodative and focusing ability of the eye while minimizing the side effects from each compound.

11 Claims, 6 Drawing Sheets

(56) References Cited

U.S. PATENT DOCUMENTS

| | | |
|---|---|---|
| 8,829,037 B2 | 9/2014 | Sharma |
| 9,089,562 B2 | 7/2015 | Horn et al. |
| 9,301,933 B2 | 4/2016 | Abad |
| 2002/0035264 A1 | 3/2002 | Kararli et al. |
| 2004/0078009 A1 | 4/2004 | Lin |
| 2005/0119262 A1 | 6/2005 | Wax |
| 2005/0205101 A1 | 9/2005 | Lin |
| 2006/0177430 A1 | 8/2006 | Bhushan et al. |
| 2009/0156606 A1 | 6/2009 | Sharma |
| 2010/0016395 A1 | 1/2010 | Benozzi |
| 2010/0298335 A1 | 11/2010 | Kaufman |
| 2011/0091459 A1 | 4/2011 | Gant et al. |
| 2011/0104155 A1 | 5/2011 | Rekik |
| 2011/0152274 A1 | 6/2011 | Kaufman |
| 2012/0208858 A1 | 8/2012 | Shanler et al. |
| 2012/0225918 A1 | 9/2012 | Silverberg |
| 2013/0096131 A1 | 4/2013 | Sharma |
| 2013/0116215 A1 | 5/2013 | Coma et al. |
| 2013/0317036 A1 | 11/2013 | Rekik |
| 2014/0024642 A1 | 1/2014 | Vejarano Restrepo |

FOREIGN PATENT DOCUMENTS

| | | |
|---|---|---|
| EP | 1938839 B1 | 8/2009 |
| EP | 2886113 | 6/2015 |
| WO | 9325199 A1 | 12/1993 |
| WO | 2005021004 | 3/2005 |
| WO | 2008075149 | 6/2008 |
| WO | 2009077736 A2 | 6/2009 |
| WO | 2009077736 A3 | 6/2009 |
| WO | 2009077736 A4 | 6/2009 |
| WO | 2009112878 | 9/2009 |
| WO | 2010125416 | 11/2010 |
| WO | 20100135731 A1 | 11/2010 |
| WO | 2014015183 | 1/2014 |

OTHER PUBLICATIONS

Duzman et al., Efficacy and Safety of Topical Oxymetazoline in Treating Allergic and Environmental Conjunctivitis Ann. Ophthalmol., vol. 18, 1986, pp. 28-31.

Evans et al., Agonist-specific coupling of G-protein-coupled receptors to second-messenger systems, Progress in Brain Research, vol. 106, 1995, pp. 259-268.

Gilmartin et al., Reversal of tropicamide mydriasis with single instillations of pilocarpine can induce sustantial pseudo-myopia in young adults, Ophthalmic and Physiological Optics, vol. 15, No. 5, pp. 475-479.

Fitzgerald et al., The Coxibs, Selective Inhibitors of Cyclooxygenase-2, The New England Journal of Medicine, vol. 345, No. 6, Aug. 9, 2001, pp. 433-442.

Fox et al., Oxymetazoline in the Treatment of Allergic and Non-Infectious Conjunctivitis, J. Int. Med. Res., vol. 7, 1979, pp. 528-530.

Fuder, Hermann, Functional Consequences of Prejunctional Receptor Activation or Blockade in the Iris, Journal of Ocular Pharmacology, vol. 10, No. 1, pp. 109-123.

Glasser, A., Accommodation and Presbyopia, In: Adler's Physiology of the Eye, 2003, University of Houston, Houston, TX.

Hickenbotham et al., Comparison of spherical aberration and small-pupil profiles in improving depth of focus for presbyopic corrections, J. Cataract Refract. Surg., vol. 38, No. 12, Dec. 2012, pp. 2071-2079.

Adamczyk et al., Antiallergy Drugs and Decongestants, Chpt. 13, Clinical Ocular Pharmacology, Fifth Edition, pp. 299-311.

Kenakin, Terry, Agonist-receptor efficacy II: agonist trafficking of receptor signals, Trends in Pharmacological Sciences, vol. 16, 1995 pp. 232-238.

Konigsberg, William, Reduction of Disulfide Bonds in Proteins with Dithiothreitol, Methods in Enzymology, Academic Press, New York, NY, USA, vol. XXV, 1972, pp. 185-188.

Lachman, Leon, Antioxidants and Chelating Agents as Stabilizers in Liquid Dosage Forms—Part 1, Drug and Cosmetic Industry, vol. 102, 1968, pp. 36-38, 40 and 146-148.

Miller et al., Passive and Oxymetazoline-Enhanced Delivery With a Lens Device: Pharmacokinetics and Efficacy Studies with Rabbits, Journal of Ocular Pharmacology and Therapeutics, vol. 24, No. 4, 2008, pp. 385-391.

Minyan et al., Evidence for a non-adrenoreceptor, imidazonine-mediated contractile response to oxymetazoline in the porcine isolated rectal artery, British Journal of Pharmacology, vol. 132, 2001, pp. 1359-1363.

Novitskaya et al., Effect of some ophthalmic medications on pupil size: a literature review, Can. J. Ophthalmol., vol. 44, No. 2, 2009, pp. 193-197.

Ostrin et al., Accommodation measurements in a prepresbyopic and presbyopic population, J. Cataract Refract. Surg., vol. 30, 2004, pp. 1435-1444.

Ottino et al., Corneal stimulation of MMP-1, -9 and uPA by platelet-activating factor is mediated by cyclooxygenase-2 metabolites, Current Eye Research, vol. 23, No. 2, 2001, pp. 77-85.

Patil et al., Antimuscarinic Action of Oxymetazoline on Human Intraocular Muscles, Journal of Ocular Pharmacology and Therapeutics, vol. 20, No. 4, 2004, pp. 328-332.

Samson et al., Safety and toleration of oxymetazoline ophthalmic solution, Pharmatherapeutica, vol. 2, No. 6, 1980, pp. 347-352.

Starke, Klaus, α Adrenoreceptor Subclassification, Rev. Physiol. Biochem. Pharmacol., vol. 88, 1981, pp. 199-236.

Thorin, Eric, Functional cross-talk between endothelial muscarinic and α2-adrenergic receptors in rabbit cerebral artieries, Brit. J. Pharmacol., vol. 125, 1998, pp. 1188-1193.

Vajpayee et al., Management of benign red eye (evaluation of topical oxymetazoline-a double masked study), Indian Journal of Ophthalmology, 1986, pp. 33-36.

Wang et al., Review of Excipients and pHs for Parenteral Products Used in the United States, Journal of teh Parenteral Drug Association, vol. 34, No. 6, 1980, pp. 452-462.

Wang et al., Supplement 1988, Parenteral Formulations of Proteins and Peptides: Stability and Stabilizers, J. Parent. Sci. and Tech., 42:S4-S26.

Patent Cooperation Treaty, International Search Report, International Application No. PCT/IB2012/002335, May 14, 2013.

Tada, Yoshifumi et al., Non-steroidal antiinflammatory drug—Management of gastrointestinal complications and inhibition of COX-2, Nippon Rinsho, 1999, 419-424, 27 (2) (English abstract only).

Figure 1. Pilocarpine + Oxymetazoline. Near vision over time.

Jaeger Equivalent: J1+ = 0, J1 = 1, J3 = 3, J5 = 5

Figure 2. Pilocarpine + Oxymetazoline. Distance vision over time.

LogMAR Equivalent: 20/20 = 0, 20/25 = 1, 20/30 = 2, 20/40 = 3

Figure 3. Pilocarpine + Oxymetazoline vs. Pilocarpine alone.

Near vision over time

Jaeger Equivalent: J1+ = 0, J1 = 1, J3 = 3, J5 = 5

Figure 4. Pilocarpine + Oxymetazoline vs. Pilocarpine alone.
Distance vision over time LogMAR Equivalent: 20/20 = 0. 20/25 = 1. 20/30 = 2. 20/40 = 3

Figure 5. Pilocarpine + Meloxicam. Near vision over time.

Jaeger Equivalent: J1+ = 0, J1 = 1, J3 = 3, J5 = 5

COMPOSITIONS AND METHODS FOR TREATING PRESBYOPIA, MILD HYPEROPIA, AND IRREGULAR ASTIGMATISM

This is a national stage application under 35 U.S.C §371 of PCT Patent Application Ser. No. PCT/IB2012/002335, filed Sep. 19, 2012, all of which claim the benefit of U.S. Provisional Patent Application Ser. No. 61/536,921, filed Sep. 20, 2011, the disclosures of which are hereby incorporated in their entirety herein by reference.

BACKGROUND

The normal (emmetropic) eye has a refractive power and axial length which are balanced with each other. Seeing distant objects sharply occurs by the light rays passing through the eye's optical system in a passive way without any active muscular contraction. In the normal eye, only the focusing of near objects requires an active muscular increase in the refractive power of the eye. The hyperopic eye is either shorter or has a weaker refractive power and hence needs an active muscular mechanism to focus on distant objects (beyond about 6 meters) that has to be increased even further to focus on near objects. The myopic eye is either longer or has a too powerful refractive power, so distant objects appear blurry but near objects are in perfect focus without any active muscular intervention.

The active muscular mechanism of focusing of the human and primate eye involves the change in shape and position of the crystalline lens, produced by the contraction of the ciliary muscle of the eye that increases further the baseline refractive power of the eye. Starting in childhood, the crystalline lens begins to gradually lose its malleability and its capacity to change shape and position in response to the contraction of the ciliary muscle. From an optical standpoint, hyperopic eyes are generally affected first by this loss of malleability due to the need to increase the refractive power of the hyperopic eye to see clearly. Around age 40, the loss of malleability begins to affect normal eyes when they are unable to focus on near objects (40 centimeters or less from the eye) in a comfortable manner in a process called presbyopia.

In the eye, the ciliary muscle is under the control of the parasympathetic nervous system via acetylcholine and its muscarinic receptors. The sympathetic nervous system plays a secondary (regulatory) role via its alpha and beta receptors. Muscarinic agonists or stimulants increase the contraction of the ciliary muscle and hence increase the refractive power of the eye. From the sympathetic standpoint, alpha-2 and beta-2 stimulants produce the same contracting action on the ciliary muscle in part by allowing the parasympathetic system to work in an unopposed manner. If this stimulation is strong enough, some of the loss of the ability of the crystalline lens to change shape and position that normally occurs with age could be overcome while this stimulation is in place.

Another mechanism to be taken into account for treating presbyopia, is the effect on the dilating and sphincter muscles of the iris that change the diameter of the pupil. The iris sphincter is mainly under parasympathetic control via muscarinic receptors, although the sphincter does have some alpha and beta receptors. The iris dilating muscle is under sympathetic control, mainly alpha-1 and alpha-2 receptors with the alpha-1 stimulants producing dilation and the alpha-2 stimulants limiting dilation. The depth of the visual field of the eye could be increased by decreasing the diameter of the pupil. This is analogous to a photographic camera in which the depth of field increases as the diaphragm is closed. Hence the use of a muscarinic agonist (activating the iris sphincter) or an alpha-2 agonist (relaxing the dilating muscle of the iris) may constrict the pupil thereby increasing the depth of focus of the eye.

The most common way to correct presbyopia is by using reading glasses or bifocal glasses. There are also special contact lenses designed for this purpose. Several surgical treatments have also been devised for the treatment of presbyopia including special intraocular lenses, laser reshaping of the cornea, and scleral expansors. Exercises have been proposed as a way to delay the onset of presbyopia. However, the effectiveness of exercise in treating or preventing presbyopia has not been demonstrated in medical research. Pharmacological treatments for presbyopia have been proposed. However, many of these treatments have proven to be ineffective and/or have undesirable side effects.

Pilocarpine is an acetylcholine analog that acts as an agonist on the muscarinic receptors of the parasympathetic nervous system. It is a well-known antiglaucoma medication which has been in use as an ophthalmic preparation for more than 100 years. It is also used in an oral form to treat dry mouth/eyes. U.S. Pat. Nos. 6,291,466 and 6,410,544 describe one patient that had a decrease in his/her hyperopia of less than half a diopter after the application of 0.3% topical pilocarpine. A myopic patient had a decrease in his myopia after the same dose of pilocarpine which was counterintuitive.

U.S. Application No. 2010/0016395 A1 reports being able to increase the dose of pilocarpine to 1% to 2% by adding the non-steroidal anti-inflammatory agent diclofenac, but at a concentration that was five times more concentrated than that approved by the FDA. Congdon et al. reported that diclofenac is associated with serious side effects such as persistent epithelial defects, corneal melting, and corneal perforation, (Congdon et al., 2001, Corneal complications associated with topical ophthalmic use of nonsteroidal anti-inflammatory drugs, *Ophthalmology*, 27:622-631)

WO 2009/077736 discloses a combination of pilocarpine and dapiprazole (or thymoxamine) and pilocarpine and brimonidine (or iopidine) to treat defects of visual acuity, presbyopia, myopia, hypermetropia, low night vision, and astigmatism. The combinations listed are pilocarpine and dapiprazole (or thymoxamine), and pilocarpine and brimonidine (or iopidine). The combination of pilocarpine and dapiprazole produced red and irritated eyes (WO 2009/077736) and topical administration of brimonidine is known to those in the art to produce lightheadedness, dizziness, dry mouth, tachycardia, and stomach upset, among other side effects, which limits its usage even among patients using it for a severe eye condition such as glaucoma.

Although more than 75 molecules have been disclosed for the medical treatment of presbyopia, no clinically effective preparations suitable for use by the general public without unreasonable side effects have been found.

SUMMARY OF THE INVENTION

Compositions and methods for treating ocular conditions, including presbyopia and mild hyperopia, up to about 4.00 diopters, or more in very young patients, irregular astigmatism, hyperopic accommodative esotropia, and glaucoma, are disclosed. The compositions of the present invention include a cholinergic agent, such as a muscarinic acetylcholine receptor $M_3$ agonist, and an alpha-stimulant agonist having an imidazoline group or a non-steroidal anti-inflammatory agent (NSAID) having COX-2 selectivity. Examples of muscarinic acetylcholine receptor $M_3$ agonists include pilocarpine, acetylcholine, pilocarpidine, bethanechol, carbachol, and oxotremorine. Examples of alpha-stimulant agonists having an imidazoline group include oxymethazoline, naphazoline, tetrahydrozoline, and xylometazoline. Examples of NSAIDs with COX-2 selectivity include meloxicam, celecoxib, rofecoxib, vaidecoxib, parecoxib, etoricoxib, nimesulide, etodolac and nabumetone.

The compositions of the present invention were surprisingly and unexpectedly found to potentiate the action of and decrease the side effects of a cholinergic agent such as pilocarpine, such that a cholinergic agent can be effectively used in combination with an alpha-stimulant agonist having an imidazoline group or a non-steroidal anti-inflammatory agent (NSAID) having COX-2 selectivity to contract the ciliary and pupillary sphincter muscles for treating ocular conditions, such as presbyopia, mild hyperopia, and irregular astigmatism, hyperopic accommodative esotropia and glaucoma, without the patient experiencing the undesirable side effects normally associated with pilocarpine therapy. The present invention can also be used to potentiate or to enhance interventions that retard, reverse or modify the aging process of the crystalline lens and its surrounding tissues. Unlike previous compositions disclosed in the prior art, it is believed that the compositions of the present invention can safely be used by patients for treatment of ocular conditions, including presbyopia, mild hyperopia, irregular astigmatism, hyperopic accommodative esotropia, and glaucoma, on a chronic basis.

DETAILED DESCRIPTION OF THE INVENTION

Definitions

The phrase "a" or "an" entity as used herein refers to one or more of that unity) for example, a compound refers to one or more compounds or at least one compound. As such, the terms "a" (or "an"), "one or more", and "at least one" can be used interchangeably herein.

As used herein, a "composition" refers to a material suitable for administration to an eye of a subject. Compositions may include a polymeric drug delivery system if desired. Compositions may comprise a liquid carrier. The term can also be used to refer to materials such as solutions, suspensions, emulsions, and the like.

The term "therapeutically effective amount" as used herein, refers to the level or amount of agent needed to treat an ocular condition, without causing significant negative or adverse side effects to the eye or a region of the eye.

As used herein, an "ocular condition" is a disease, ailment or condition which affects or involves the eye or one of the parts or regions of the eye, including the eyeball and the tissues and fluids which constitute the eyeball, the periocular muscles (such as the oblique and rectus muscles) and the portion of the optic nerve which is within or adjacent to the eyeball. Examples of an ocular condition include presbyopia and mild hyperopia, irregular astigmatism, hyperopic accommodative esotropia, and glaucoma.

The following terms are ophthalmic terms commonly used by those of skill in the art. "OD" stands for oculus dexter and means right eye. "OS" stands for oculus sinister and means left eye, "UDVA" stands for unaided distance visual acuity. "UNVA" stands for unaided near visual acuity. "Sph" is the sphere, or the amount of magnification/demagnification that the eye needs to see properly. A negative sphere indicates myopia, and a positive sphere indicates hyperopia. "Cyl" is the cylinder, which is a measure of astigmatism. "Pre" indicates the condition of the eye prior to treatment, 1 h indicates the condition of the eye 1 hour after treatment, 4 h indicates the condition of the eye 4 hours after treatment, and 6 h indicates the condition of the eye 6 hours after treatment. "Sph Eq" is the spherical equivalent.

Measurements on the Jaeger scale, a near vision scale, are used and described herein. Some examples of Jaeger scale values used herein include the following: J1+ is fine "normal" near vision (equivalent to 20/20 in Snellen terms), which is the ability to read the bottom line (in 3-point font letters) on a near vision eye chart; J1 is good near vision (equivalent to 20/25 in Snellen terms), which is the ability to read the next-to-bottom line (in 4-point font letters) on a near vision eye chart; J2 and J3 are fair and functional near vision, respectively (equivalent to 20/30 and 20/40, respectively, in Snellen terms), which is the ability to read lines 3 and 4, respectively, from the bottom on a near vision eye chart, wherein J3 is "reading vision" for 6-point font letters.

"LogMAR" is a commonly used visual acuity scale, expressed as the (decadic) logarithm of the minimum angle of resolution. LogMAR scale converts the geometric sequence of a traditional chart to a linear scale.

MODES FOR CARRYING OUT THE INVENTION

Alpha-stimulant agents having an imidazoline group, such as oxymetazoline, naphazoline, and tetrahydrozoline, have been used on a wide scale as self-prescribing medications, available over the counter in the United States since the 1970's for ocular redness/irritation with side effects reported very rarely. Xylometazoline, another derivative of imidazoline, has been used as a nasal decongestant. Despite widespread use of these agents by the general public, these agents have not been previously used to treat ocular conditions, such as presbyopia, because of their lack of a significant clinical effect when used in isolation.

Pilocarpine, a cholinergic agent, has been used as an isolated medication for the treatment of presbyopia and mild hyperopia, but has not been very effective because topical concentrations below 0.5% produce minimal effect in the accommodation of the eye and concentrations above 0.5% are not tolerated due to side effects such as red eyes, ocular pain, brow ache, and headache. In addition, at concentrations of pilocarpine effective enough to improve the reading ability of the presbyopic patient, the eye is rendered so myopic that there is a significant decrease in the eye's distance vision (Gilmartin et al., 1995, *Ophthalmic and Physiological Optics*, Pergamon Press, Oxford, GB, 15(5): 475-479).

Non-steroidal anti-inflammatory agents (NSAIDs) inhibit the enzyme cyclooxygenase that produces prostaglandins. This enzyme has two forms: cyclooxygenase-1 (COX-1) that is supposed to have "resident" and "housekeeping" functions and cyclooxygenase-2 (COX-2) that is up regulated in cases of inflammation and cancer. Agents that selectively inhibit COX-2, as opposed to both COX-1 and COX-2, are believed to block inflammation without affecting the normal homeostatic body mechanisms. (Fitzgerald G A and Patrono C. *The caxibs, selective inhibitors of cyclooxygenase-2*. NEJM 2001; 345:433-442). While this is true for gastrointestinal mucosal protection, side effects such as thrombotic events or renal damage have been reported, such as in the case of oral rofecoxib. The inhibition of COX-2 products at the corneal level decreases collagenases that increase a known ocular side effect of NSAIDs such as corneal melting (Ottino P and Bazan H E. *Corneal stimulation of MMP-1, -9 and uPA by platelet-activating factor is mediated by cyclooxygenase-2 metabolites*. Curr Eye Res. 2001 August; 23(2):77-85).

The compositions of the present invention have been surprisingly and unexpectedly found to potentiate the action of and decrease the side effects of a cholinergic agent, such as pilocarpine, such that a cholinergic agent can be effectively used in combination with an alpha-stimulant agonist having an imidazoline group or a NSAID having COX-2 selectivity to contract the ciliary and pupillary muscles for treating an ocular condition, such as presbyopia, mild hyperopia, irregular astigmatism, hyperopic accommodative esotropia, or glaucoma, without the patient experiencing the undesirable side effects normally associated with pilocarpine therapy, in addition, alpha-stimulant agents having an imidazoline group, which were previously found to lack significant clinical effect for treating ocular conditions, have a synergistic effect in combination with a cholinergic agent, such as pilocarpine. Although not wishing to be bound by any particular theory, it is believed that the synergistic effect is due post-receptor cross-talk between muscarinic and adrenergic receptors, possibly via G proteins, resulting in the observed novel interaction of imidazole compounds and muscarinic agonists. Unlike previous compositions disclosed in the prior art, the compositions of the present invention can safely be used by patients for treatment of ocular conditions, such as presbyopia, mild hyperopia, and irregular astigmatism, hyperopic accommodative esotropia, or glaucoma on a chronic basis. The present invention can also be used to potentiate or to enhance interventions that retard, reverse or modify the aging process of the crystalline lens and its surrounding tissues.

The compositions of the present invention include a cholinergic agent in combination with an alpha-stimulant agonist having an imidazoline group or a NSAID having COX-2 selectivity. The cholinergic agent can be a muscarinic acetylcholine receptor $M_3$ agonist that acts on the ciliary muscle of the eye and causes it to contract. Pilocarpine and carbachol are examples of a suitable muscarinic acetylcholine receptor $M_3$ agonist. Additional examples include acetylcholine, bethanechol, oxotremorine, pilocarpidine, and the like. In an embodiment, the cholinergic agent is pilocarpine.

Examples of an alpha-stimulant agonist having an imidazoline group suitable for use in the compositions of the present invention include oxymetazoline, naphazoline, tetrahydrozoline, tramazoline, xylometazoline, and the like. In an embodiment, the alpha-stimulant agonist comprises one or more of oxymetazoline, naphazoline, tetrahydrozoline, tramazoline, and xylometazoline. In an embodiment, the alpha-stimulant agonist comprises oxymethazoline. In another embodiment, the alpha-stimulant agonist comprises naphazoline, in yet another embodiment, the alpha-stimulant agonist comprises tetrahydrozoline.

Examples of a NSAID having COX-2 selectivity include meloxicam, celecoxib, rofecoxib, valdecoxib, parecoxib, etoricoxib, nimesulide etodolac and nabumetone and the like. In an embodiment, the NSAID comprises one or more of meloxicam, celecoxib, rofecoxib, valdecoxib, parecoxib, etoricoxib, nimesulide, etodolac and nabumetone. In another embodiment, the NSAID comprises meloxicam.

The cholinergic agent in combination with the alpha-stimulant agonist having an imidazoline group or the NSAID having COX-2 selectivity potentiate the effects of the cholinergic agent and the alpha-stimulant agonist or the NSAID, contracting the ciliary muscle and reducing the pupillary diameter effectively treating ocular conditions, such as presbyopia, mild hyperopia, and irregular astigmatism, hyperopic accommodative esotropia, or glaucoma. The combinations described herein also decrease the side effects of the cholinergic agent without adding significant side effects from the alpha-stimulant agonist or the NSAID, making it easier for patients to tolerate chronic usage of the compositions of the invention.

By administering the cholinergic agent in combination with the alpha-stimulant agonist or the NSAID, the agents act simultaneously and precisely on the ocular receptors modulating each other's effects. When the agents are applied separately on a sequential basis there is saturation of the receptors by one of the agents before the other agent is applied leading to erratic clinical responses. This can be further compounded by the washout effect of applying one drop of the second agent in the conjunctival cul-de-sac after the first agent, leading to unknown concentrations of the active compounds being delivered to the eye.

The compositions of the invention are suitable for ophthalmic use. The compositions generally include from about 0.01% to about 4% w/w cholinergic agent and either from about 0.01% to about 0.5% w/w alpha-stimulant agonist having imidazoline group, or from about 0.01% to about 2% w/w NSAID having COX-2 selectivity, or both. The compositions can include any of the concentrations of alpha-stimulant agonist having an imidazoline group and/or NSAID having COX-2 selectivity as described herein in combination with any of the concentrations of cholinergic agent as described herein.

According to an embodiment, ophthalmic preparations of the composition comprise from about 0.01% to about 4% w/w cholinergic agent, such as pilocarpine or carbachol. In another embodiment, ophthalmic preparations of the composition comprise from about 0.01% to about 3.5% cholinergic agent. In yet another embodiment, ophthalmic preparations of the composition comprise from about 0.01% to about 3% w/w cholinergic agent. In yet another embodiment, ophthalmic preparations of the composition comprise from about 0.01% to about 2.5% w/w cholinergic agent. In yet another embodiment, ophthalmic preparations of the composition comprise from about 0.01% to about 2% w/w cholinergic agent. In yet another embodiment, ophthalmic preparations of the composition comprise from about 0.1% to about 2.0% w/w cholinergic agent.

According to an embodiment, ophthalmic preparations of the composition comprise from about 0.01% to about 0.5% w/w alpha-stimulant agonist having an imidazoline group, such as oxymetazoline. In another embodiment, ophthalmic preparations of the composition comprise from about 0.01% to about 0.25% w/w alpha-stimulant agonist having an imidazoline group. According to a preferred embodiment, ophthalmic preparations of the composition comprise from about 0.01% to about 0.1% w/w alpha-stimulant agonist having an imidazoline group. According to another preferred embodiment, ophthalmic preparations of the composition comprise from about 0.01% to about 0.05% w/w alpha-stimulant agonist having an imidazoline group According to another preferred embodiment, ophthalmic preparations of the composition comprise about 0.025% w/w alpha-stimulant agonist having an imidazoline group.

According to an embodiment, ophthalmic preparations of the composition comprise from about 0.01% to about 2% w/w NSAID having COX-2 selectivity, such as meloxicam. In another embodiment, ophthalmic preparations of the composition comprise from about 0.01% to about 1% w/w NSAID having COX-2 selectivity. In another embodiment, ophthalmic preparations of the composition comprise from about 0.01% to about 0.5% w/w NSAID having COX-2 selectivity. According to a preferred embodiment, ophthalmic preparations of the composition comprise from about 0.01% to about 0.2% w/w NSAID having COX-2 selectivity. According to another preferred embodiment, ophthalmic preparations of the composition comprise from about 0.01% to about 0.1% w/w NSAID having COX-2 selectivity.

In one aspect, ophthalmic preparations of the compositions of the invention can include from about 0.01% to about 4%, from about 0.01% to about 3.5%, from about 0.01% to about 3.0%, or from about 0.01% to about 2.5% w/w cholinergic agent and from about 0.01% to about 0.2% w/w alpha-stimulant agonist having an imidazoline group. In an embodiment, the composition comprises from about 0.01% to about 2% w/w cholinergic agent and from about 0.01% to about 0.2% w/w alpha-stimulant agonist having an imidazoline group. In an embodiment, the composition comprises from about 0.5% to about 1.5% w/w cholinergic agent and from about 0.02% to about 0.1% alpha-stimulant agonist. In another embodiment, the composition comprises from about 0.9% to about 1.1% w/w cholinergic agent and from about 0.0125% to about 0.5% w/w alpha-stimulant agonist. The cholinergic agent can be a muscarinic acetylcholine receptor $M_3$ agonist that acts on the ciliary muscle of the eye and causes it to contract. Pilocarpine and carbachol are examples of a suitable muscarinic acetylcholine receptor $M_3$ agonist. Additional examples include acetylcholine, bethanechol, oxotremorine, pilocarpidine and the like. Examples of an alpha-stimulant agonist having an imidazoline group include oxymetnoline, naphazoline, tetrahydrozoline, tramazoline, xylometazoline, and the like.

In embodiments, the composition comprises pilocarpine and oxymetazoline. The dosage of pilocarpine in these compositions can range from about 0.01% to about 2% w/w and the dosage of oxymetazoline can range from about 0.01% to about 0.1% w/w. In an embodiment, the composition comprises a concentration of pilocarpine from about 0.5% to about 0.9% w/w and a concentration of oxymetazoline from about 0.01% to about 0.024% w/w. In another embodiment, the composition comprises a concentration of pilocarpine from about 1.1% to about 2% w/w and a concentration of oxymetazoline from about 0.026% to about 0.1% w/w, In yet another embodiment, the composition comprises a concentration of pilocarpine of out 1% w/w and a concentration of oxymetazoline of about 0.0125% w/w.

In embodiments, the composition comprises pilocarpine and naphazoline. The dosage of pilocarpine in these compositions can range from about 0.01% to about 2% w/w and the dosage of naphazoline can range from about 0.01% to about 0.2% w/w. In an embodiment, the composition comprises a concentration of pilocarpine, from about 0.01% to about 0.9% w/w and a concentration of naphazoline from about 0.01% to about 0.09% w/w. In another embodiment, the composition comprises a concentration of pilocarpine from about 1.1% to about 2% w/w and a concentration of naphazoline from about 0.11% to about 0.2% w/w. In yet another embodiment, the composition comprises a concentration of pilocarpine of about 1% w/w and a concentration of naphazoline of about 0.1% w/w.

In embodiments, the composition comprises pilocarpine and tetrahydrozoline. The dosage of pilocarpine in these compositions ranges from about 0.01% to about 2% w/w and the dosage of tetrahydrozoline ranges from about 0.01 to about 0.1% w/w. In an embodiment, the composition comprises a concentration of pilocarpine from about 0.01% to about 0.9% w/w and a concentration of tetrahydrozoline from about 0.01% to about 0.04% w/w. In another embodiment, the composition comprises a concentration of pilocarpine from about 1.1% to about 2% w/w and a concentration of tetrahydrozoline from about 0.06% to about 0.1% w/w. In yet another embodiment, the composition comprises a concentration of pilocarpine of about 1% w/w and a concentration of tetrahydrozoline of about 0.05% w/w.

Other suitable alpha-stimulant agonists having an imidazoline group, such as tramazoline and xylometazoline can be formulated in combination with pilocarpine at the dosages and concentration ranges disclosed herein for oxymetazoline, naphazoline, or tetrahydrozoline. In an embodiment, the tramazoline is present from about 0.03% w/w to about 0.12% w/w. In another embodiment, pilocarpine, at concentrations disclosed herein, is combined with tramazoline at a concentration of about 0.06% w/w. In an embodiment, the xylometazoline is present from about 0.01% w/w to about 0.10% w/w. In another embodiment, pilocarpine, at concentrations disclosed herein, is combined with xylometazoline at a concentration of about 0.025% w/w. Other suitable cholinergic agents, such as acetyleholine, bethanechol, carhachol oxotremorine, and pilocarpidine, can be formulated in combination with oxymetazoline, naphazoline, tetrahydrozoline, trantazoline, or xylometazoline at the dosages and concentration ranges disclosed herein for pilocarpine.

In another aspect, ophthalmic preparations of the compositions of the invention can include from about 0.01% to about 4%, from about 0.01% to about 3.5%, from about 0.01% to about 3.0%, or from about 0.01% to about 2.5% w/w cholinergic agent and from about 0.001% to about 2% w/w NSAID having COX-2 selectivity. In an embodiment, the composition comprises from about 0.01% to about 2% w/w cholinergic agent and from about 0.001% to about 2% w/w NSAID having COX-2 selectivity. In an embodiment, the composition comprises from about 0.5% to about 1.5% w/w cholinergic agent and from about 0.1 to about 1% of the NSAID. In another embodiment, the composition comprises from about 0.9% to about 1.1% w/w cholinergic agent and from about 0.01% to about 0.1% w/w of the NSAID. The cholinergic agent can be a muscarinic acetylcholine receptor $M_3$ agonist that acts on the ciliary muscle of the eye and causes it to contract. Pilocarpine and carbachol are examples of a suitable muscarinic acetylcholine receptor $M_3$ agonist. Additional examples include acetylcholine, bethanechol, oxotremorine, pilocatpidine, and the like. Examples of a NSAID having COX-2 selectivity include meloxicam, celecoxib, rofecoxib, valdecoxib, parecoxib, etoricoxib, nimesulide, etodolac, nabumetone and the like.

In embodiments, the composition comprises pilocarpine and meloxicam. The dosage of pilocarpine in these compositions ranges from about 0.01% to about 2% w/w and the dosages of meloxicam ranges from about 0.001% to about 2% w/w. In an embodiment, the composition comprises a concentration of pilocarpine from about 0.01% to about 0.9% w/w and a concentration of meloxicam from about 0.01% to about 1% w/w. In another embodiment, the composition comprises a concentration of pilocarpine from about 1.1% to about 2% w/w and a concentration of meloxicam from about 0.1% to about 0.5% w/w. In yet another embodiment, the composition comprises a concentration of pilocarpine of about 1% w/w and a concentration of meloxicam of about 0.03% w/w.

Other suitable NSAIDs having COX-2 selectivity, such as celecoxib, rofecoxib, valdecoxib, parecoxib, etoricoxib, nimesulide, etodolac or nabumetone can be formulated in combination with pilocarpine at the dosages and concentration ranges disclosed herein for meloxicam. Other suitable cholinergic agents, such as acetylcholine, bethanechol, carbachol, oxotremorine, and pilocarpidine, can be formulated in combination with meloxicam, celecoxib, rofecoxib, valdecoxib, parecoxib, etoricoxib, nimesulide, etodolac or nabumetone a the dosages and concentration ranges disclosed herein for pilocarpine. In an embodiment, the $M_3$ agonist carbachol is present at a concentration of about 0.1% w/w to about 4% w/w or about 0.1% w/w to about 3% w/w in combination with an alpha-stimulant agonist having an imidazoline group or a non-steroidal anti-inflammatory agent (NSAID) having COX-2 selectivity, wherein the alpha-stimulant or NSAID is used at a concentration as described in one of the above embodiments. In another embodiment, the $M_3$ agonist carbachol is present at a concentration of about 2.5% w/w in combination with an alpha-stimulant agonist having an imidazoline group or a non-steroidal anti-inflammatory agent (NSAID) having COX-2 selectivity, wherein the alpha-stimulant or NSAID is used at a concentration as described in one of the above embodiments.

The compositions of the invention can be customized for a patient based on the patient's need for vision correction and the patient's responsiveness to the composition. For example, patients with mild forms of hyperopia or presbyopia in need of minor correction may be provided with a composition with lower a concentration of cholinergic agent. On the other hand, patients with more severe hyperopia or presbyopia may be provided with a composition with a higher concentration of cholinergic agent. In general, younger patients (e.g. patients less than forty years old) may experience hyperopia or early symptoms of presbyopia and may only need minor correction, whereas older patients (e.g. patients in their fillies and above) may experience more pronounced symptoms of presbyopia era combination of hyperopia and presbyopia and may need more correction. Some patients may need a lower concentration of cholinergic agent because they respond more strongly to the medication. For example, very young patients (e.g. children) may respond more strongly than older patients, and may therefore benefit from a lower concentration of cholinergic agent.

According to exemplary embodiments, a composition for treating patients with very mild conditions or who respond strongly comprises from about 0.1% to about 0.5% w/w cholinergic agent, such as pilocarpine, or from about 0.2% to about 0.4% w/w cholinergic agent, or about 0.3% w/w cholinergic agent. A composition for treating patients with mild conditions or whose vision could alternatively be corrected with eye glasses having about +0.5 D to about +1.0 D, or about +0.75 D lenses may comprise front about 0.3% to about 1.0% w/w cholinergic agent, such as pilocarpine, or from about 0.4% to about 0.8% w/w cholinergic agent, or from about 0.5% to about 0.7% w/w cholinergic agent, or about 0.6% w/w cholinergic agent. A composition for treating patients whose vision could alternatively be corrected with eye glasses having about +1.0 D to about +1.5 D lenses or about +1.2 D to +1.3 D lenses may comprise from about 0.8% to about 1.6% w/w cholinergic agent, such as pilocarpine, or from about 1.0% to about 1.4% w/w cholinergic agent, or from about 1.1% to about 1.3% w/w cholinergic agent, or about 1.2% w/w cholinergic agent. A composition for treating patients whose vision could alternatively be corrected with eye glasses having about +1.5 D to about +2.0 D or about +1.75 D lenses may comprise from about 1.4% to about 2.2% w/w cholinergic agent, such as pilocarpine, or from about 1.6% to about 2.0% w/w cholinergic agent, or from about 1.7% to about 1.9% w/w cholinergic agent, or about 1.8% w/w cholinergic agent.

Very young patients (e.g, children) may particularly benefit from the use of the compositions disclosed herein. Very young patients may respond more strongly to the composition, and may thus need a lower concentration of the cholinergic agent. The compositions of the invention may also be used to treat more severe conditions in very young patients than in older patients; for example, the composition may be used to treat moderate hyperopia (up to +4.0 D) in children.

The compositions of the invention may also be customized for a patient based on the patient's sensitivity to imitation or side effects. For example, a patient with more sensitivity may be provided with to composition having a higher concentration of agents that reduce redness and irritation, such as alpha-stimulant agonist having an imidazoline group or NSAID having COX-2 selectivity. According to an embodiment, a composition for treating patients with more sensitivity may comprise from about 0.05% to about 0.2% w/w alpha-stimulant agonist having an imidazoline group or NSAID having COX-2 selectivity, or a combination of both.

The compositions of the invention can further include a cyclodextrin or derivative thereof. Cyclodextrins are cyclic oligosaccharides that have less hydrophilic inner cavities and hydrophilic outer surfaces and are capable of forming non-covalent complexes with a variety of molecules. Both naturally occurring ($\alpha$-, $\beta$- and $\gamma$-) and synthetic (e.g. chemically modified hydroxyethyl-$\beta$- or sulfobutylether-$\beta$-) cyclodextrins are available. Cyclodextrins and their derivatives can be used to enhance ocular penetration of the cholinergic agent, alpha-stimulant agonist, and/or NSAID having COX-2 selectivity and decrease discomfort of the patient and ameliorate irritation upon instillation of the compositions of the invention into the eye. Examples of suitable cyclodextrins include hydrophilic cyclodextrins, such as hydroxyethyl-$\beta$-cyclodextrin and sulfobutylether-$\beta$-cyclodextrin. Cyclodextrins may also be included in the compositions of the invention to improve the solubility, bioavailability and shelf-life of the active ingredients of the compositions. According to an exemplary embodiment, the composition comprises from about 0.1% to about 4.0% of pilocarpine, from about 0.01% to about 0.1% oxymetazoline or from about 0.01% to about 0.2% meloxicam, and from about 0.1% to about 2.0% β-cyciodextrin. According to another exemplary embodiment, the composition comprises from about 0.75% to about 4% of carbachol, from about 0.01% to about 0.1% oxymetazoline or from about 0.01% to about 0.2 meloxicam, and from about 0.1% to about 2.0% β-cyclodextrin.

The compositions described herein include, without limitation, liquid-containing compositions, such as formulations, and polymeric drug delivery systems. The compositions may be understood to include solutions, suspensions, emulsions, and the like, such as other liquid-containing compositions used in ophthalmic therapies. The compositions of the invention can be incorporated into polymeric drug delivery systems including a polymeric component, and may be understood to include biodegradable polymers, biodegradable implants, non-biodegradable implants, biodegradable micropaaicies, such as biodegradable microspheres, nanoparticles and the like. The biodegradable polymers degrade in vivo wherein degradation or erosion of the polymer or polymers over time occurs concurrent with or subsequent to release of the compositions of the invention incorporated into and loaded onto the polymers. Substances of the composition with different half-lives may be incorporated in different types (size, form, composition or number) of nanoparticles, resulting in appropriate rates of release for and concentrations of each component in the treated tissue. A biodegradable polymer may be a homopolymer, a copolymer, or a polymer comprising more than two different polymeric units. The drug delivery systems disclosed herein may encompass elements in the form of tablets, wafers, rods, sheets, threads, filaments, and the like. The polymeric drug delivery systems may be solid, semisolid, or viscoelastic.

In certain embodiments, the carrier used in the present invention may be a solid support, including a polymer bead or a resin, such as a Wang resin. Supports can be solids having a degree of rigidity such as silicon, plastic, and the like. Support can also be flexible materials such as plastic or otherwise synthetic materials (such as nylon), materials made of natural polymers (such as cellulose or silk) or derivatives thereof (such as nitrocellulose) and the like. In certain embodiments the support is a porous material which can be rigid or flexible, intermeshed fibers including woven fabrics, and the like. In some embodiments, the solid support is a bead or pellet, which can be porous. In certain embodiments, the carrier or carriers may be optimized for slow or timed release of the active agents. Formulations including a polymer bead carrier, or other such carrier or carriers as described above, may be injected subconjuctivally, injected directly into the eye or the tissues surrounding the eye, may be applied topically to the eye or surrounding tissues, or may be applied in the form of a plug that is located at the nasolacrimal punctum.

In embodiments, the compositions of the invention are formulated for delivery to the eye or the tissues or fluids surrounding the eye. The compositions can be in the form of a suspension, eye drop, ointment, gel, spray, powder, slow release preparation for administration either subconjunctivally or in any other eye location, or other suitable form for administering the compositions of the invention to the eye or fluids and/or tissues surrounding the eye. The use of buffers, stabilizers, reducing agents, anti-oxidants and chelating agents in the preparation of pharmaceutical compositions is well known in the art. See, Wang et al., "*Review of Excipients and pHs for Parenteral Products Used in the United States.*" *J. Parent. Drug Assn.*, 34(6):452-462 (1980); Wang et al., "*Parenteral Formulations of Proteins and Peptides: Stability and Stabilizers,*" *J. Parent. Sci. and Tech.*, 42:S4-S26 (Supplement 1988); Lachman, et al., "*Antioxidants and Chelating Agents as Stabilizers in Liquid Dosage Forms-Part 1;*" *Drug and Cosmetic industry,* 102(1): 36-38, 40 and 146-148 (1968); Akers, M. J., "*Antioxidants in Pharmaceutical Products,*" *J. Parent. Sci. and Tech.*, 36(5):222-228 (1988); and Methods in Enzymology, Vol. XXV, Colowick and Kaplan eds., "*Reduction of Disulfide Bonds in Proteins with Dithiothreitol*" by Konigsberg, pages 185-188.

Suitable carriers include pharmaceutically acceptable carriers, excipients, or stabilizers which are nontoxic to the cell or mammal being exposed thereto at the dosages and concentrations employed. Often the physiologically acceptable carrier is sterile water or an aqueous pH buffered solution. pH regulatory agents include boric, phosphoric, acetic, carbonic, citric, sorbic acids, and the like. pH adjusting agents include acids such as hydrochloric acid or bases such as sodium or potassium hydroxide, sodium bicarbonate, and the like. Suitable physiologically or ophthalmically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™.

The compositions of the invention can include one or more preservatives such as phenol, cresol, pamaminobenzoic acid, BDSA, sorbitrate, chlorhexidine, benzalkonium chloride, sorbic and boric acids, Purite® (oxychloride compounds), Polyquad® (quaternary ammonium), polyhexamethylen biguanide, sodium perborate, and the like. Compositions intended for long-term use in chronic conditions can be formulated and packaged to minimize the use of preservatives that may irritate the eye. For example, the composition may be packaged in single-dose containers, or in containers utilizing alternative means for minimizing microbial contamination, such as membranes, valve mechanisms or silver.

The compositions can include stabilizer and viscosant agents such as one or more of microcrystalline cellulose, magnesium stearate, mannitol, sucrose, EDTA, sodium hydrogen sulfite, methyl cellulose, carboxymethyl cellulose, hydroxypropyl methylcellulose, hyaluronic acid, alginate, chonodroitin sulfate, dextran, maltodextrin, dextran sulfate, polyvinyl pyrrolidone, polyvinyl alcohol, and the like. The composition can include an emulsifier such as polysorbate 20, polysorbate 80, pluronic, triolein, soybean oil, lecithins, squalene and squalanes, sorbitan treioleate, and the like. The composition can include an antimicrobial such as phenylethyl alcohol, phenol, cresol, benzalkonim chloride, phenoxyethanol, chlorhexidine, thimerosol, and the like. Suitable thickeners include natural polysaccharides such as mannans, arabinans, alginate, hyaluronic acid, dextrose, and the like; and synthetic ones like the PEG hydrogels of low molecular weight and aforementioned suspending agents. The composition can include also osmotic agents, such as sodium chloride, potassium chloride, magnesium sulfate, calcium chloride, sodium hydrogen phosphate and the like, and humectants, such as propylene glycol, glycerine, sorbitol, mannitol, and the like.

Compositions of the invention can be used to treat an ocular condition. Preferred ocular conditions include presbyopia, mild hyperopia, irregular astigmatism (increased high order optical aberrations in the front part of the eye), hyperopic accommodative esotropia, and glaucoma (open angle; acute, subacute and chronic narrow angle; iris plateau, etc.). The present invention can also be used to potentiate or to enhance interventions that retard, reverse or modify the aging process of the crystalline lens and its surrounding tissues. The compositions of the invention are generally administered to an "ocular region" or "ocular site" of the subject undergoing treat. The subject is generally human, but can include other mammals such as dogs, cats, horses, etc. The terms "ocular region" and "ocular site" refer generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of ocular sites include the crystalline lens, the zonules, the ciliary muscle, the iris, and the pupil. Specific examples of areas of the eyeball in an ocular region include the anterior chamber, the posterior chamber, the vitreous cavity, the choroid, the suprachoroidal space, the subretinal space, the conjunctiva, the subconjunctival space, the episcleral space, the intracorneal space, the epicorneal space, the sclera, the pars plana, surgically-induced avascular regions, the macula, and the retina. The use of the compositions of the invention in both eyes of a presbyopic patient may result in optimum enhancement of near vision, but may slightly decrease distant vision. The compositions of the invention may also be used only in one eye, typically the non-dominant eye, thus improving near vision in that eye and conserving distance vision in the untreated eye. In an embodiment, a composition of the invention is administered only to the dominant eye of the patient to improve reading ability.

The compositions of the invention can increase the refractive power of the eye by up to about 4 diopters, or even more in very young patients (e.g. children). In an embodiment, the compositions of the invention increase the refractive power of the eye by up to about 0.5 diopters, about 0.75 diopters, about 1.0 diopters, about 1.25 diopters, about 1.50 diopters, about 1.75 diopters, about 2.0 diopters, about 2.5 diopters, about 3.0 diopters, about 3.5 diopters, or about 4.0 diopters. In an embodiment, the compositions of the invention increase the refractive power of the eye from about 0.5 to about 0.75 diopters, about 0.5 to about 1.0 diopters, about 0.5 to about 1.25 diopters, about 0.5 to about 1.5 diopters, about 0.5 to about 1.75 diopters, about 0.5 diopters to about 2.0 diopters, about 0.5 to about 2.5 diopters, about 0.5 diopters to about 3.0 diopters, about 0.5 diopters to about 3.5 diopters, or about 0.5 diopters to about 4.0 diopters. In an embodiment, the increase in refractive power of the eye occurs without substantially affecting the cylindrical (astigmatic) component of the eye. In an embodiment, the effect on the cylindrical component of the eye is less than 0.5 diopters. In an embodiment, the effect on astigmatismo is less than about 2.0 diopters.

In another aspect of the invention, kits for treating an ocular condition are provided. The kits generally include: a) a container, such as a syringe, tube, vial, dropper (such as would be used for eye drops), or other applicator, comprising a composition as described herein; and b) instructions for use, which may include diagrams, drawings, or photographs, in addition to text. The instructions may include steps of how to handle the material (which may include storage conditions, such as temperature ranges for storage), how to insert the material into an ocular region (optionally including diagrams, drawings, or photographs), how often to apply the composition, and what to expect from using the composition. The container may contain a single dose of the composition or multiple doses of the composition. The container may deliver the composition drop wise. The container may include tamper evident features, such as a foil or plastic seal.

EXAMPLES

For the following examples, the terms "a/an/the" include plural alternatives (at least one). The disclosed information is illustrative, and other embodiments exist and are within the scope of the present invention.

Example 1

A group of 10 patients (20 eyes) considered emmetropes or slightly hyperopic (Spherical equivalent from +0.88 D to −0.50 D with less than 1.00 D of astigmatism) was treated with a composition of the invention. Each patient had an extensive ocular examination prior to treatment that included; 1) refractive power of each eye; 2) the unaided distance visual acuity (UDVA) measured using an Snellen chart; 3) the unaided near vision (UNVA) measured at 40 centimeters using a hand-held Rosembaum chart and the Jaeger notation; and 4) the pupillary diameter measured in medium lighting (mesopic) conditions with a special infrared camera device.

Figure 1:
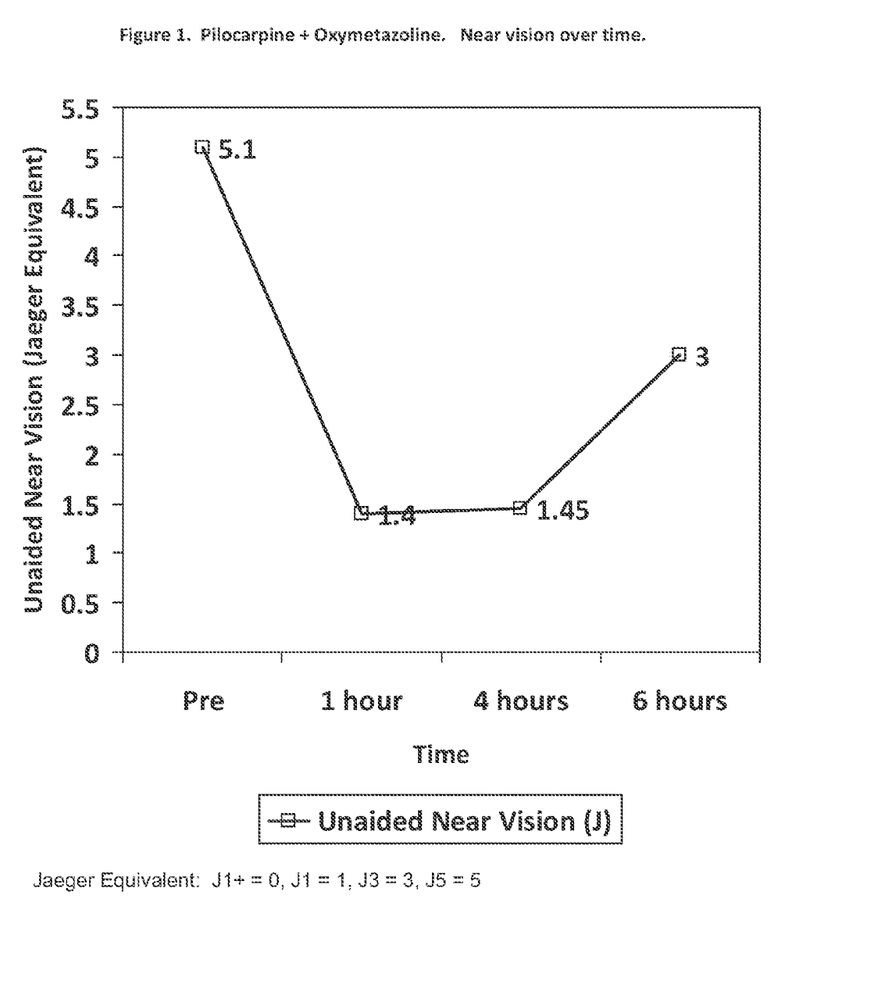
FIG. 1 shows the effect of a composition comprising pilocarpine and oxymetazoline on near vision (Jaeger Equivalent) over time.
Figure 2:
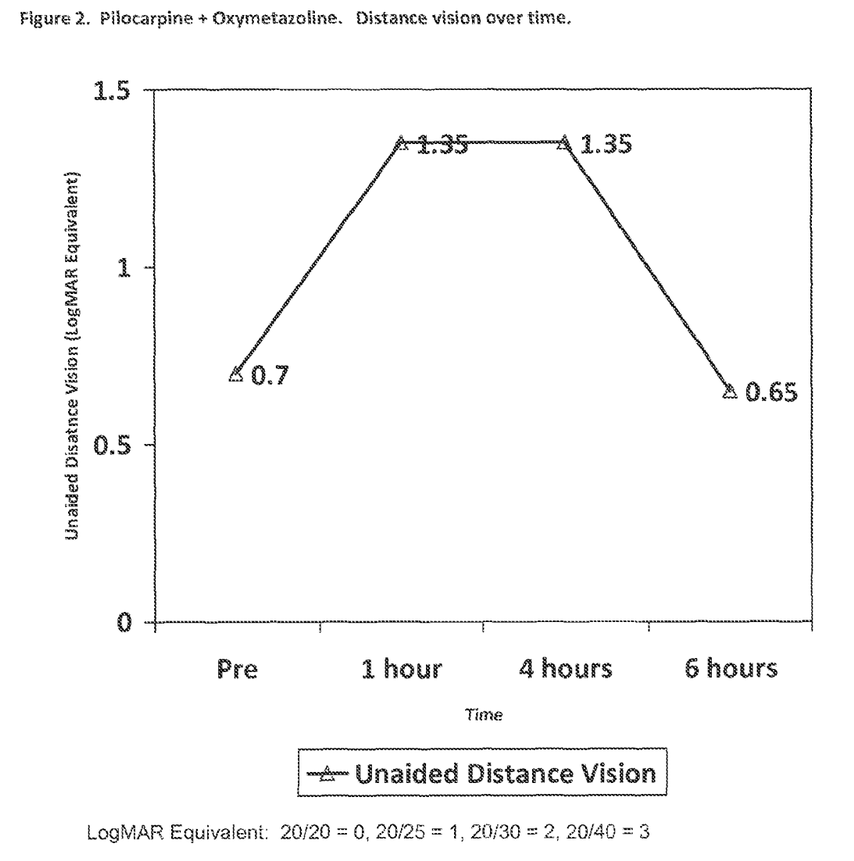
FIG. 2 shows the effect of a composition comprising pilocarpine and oxymetazoline on distance vision (LogMAR Equivalent) over time.

Three drops containing 1% pilocarpine and 0.125% oxymetazoline w/w dissolved in a solution of 0.5% sodium chloride, with carboxymethyl cellulose as a viscosant and benzalkonium chloride as preservative were instilled into each eye three times separated 5 minutes each, and the same measurements were taken one hour, four hours and six hours later (Table 1). As shown in Table 1 and FIGS. 1-2, there was an average gain of 3.7 units of unaided near visual acuity while losing 0.7 lines of uncorrected distance visual acuity at one hour after instillation. As shown in FIG. 1, there was some decay of the effect at 4 hours and it decreased to almost half at six hours. The improvement in near vision was more pronounced in younger patients and the lack of detriment of the distance vision (FIG. 2) was more marked in hyperopic patients. The refractive change was related to the sphere mostly with the cylinder remaining almost unchanged.

TABLE 1

| | | | | Pre UNVA | 1 h UNVA | 4 h UNVA | 6 h UNVA | Pre UDVA | 1 h UDVA | 4 h UDVA | 6 h UDVA |
|---|---|---|---|---|---|---|---|---|---|---|---|
| (Pilocarpine + Oxymetazoline) | | | | | | | | | | | |
| ID | Sex | Age | | | | | | | | | |
| 1 | M | 42 | OD | J2 | J1+ | J1+ | J1 | 20/20 | 20/25 | 20/25 | 20/20 |
| 1 | | | OS | J2 | J1+ | J1+ | J2 | 20/20 | 20/25 | 20/25 | 20/20 |

TABLE 1-continued (Pilocarpine + Oxymetazoline)

| | | | | | | | | | | | |
|---|---|---|---|---|---|---|---|---|---|---|---|
| 2 | F | 44 | OD | J2 | J1+ | J1+ | J2 | 20/20 | 20/30 | 20/25 | 20/20 |
| 2 | | | OS | J2 | J1+ | J1+ | J1 | 20/20 | 20/30 | 20/25 | 20/20 |
| 3 | F | 45 | OD | J3 | J1+ | J1+ | J1 | 20/20 | 20/25 | 20/30 | 20/25 |
| 3 | | | OS | J3 | J1+ | J1+ | J2 | 20/20 | 20/30 | 20/30 | 20/20 |
| 4 | M | 46 | OD | J5 | J1 | J2 | J3 | 20/25 | 20/20 | 20/20 | 20/25 |
| 4 | | | OS | J5 | J2 | J2 | J3 | 20/25 | 20/20 | 20/20 | 20/20 |
| 5 | M | 48 | OD | J3 | J1+ | J1+ | J3 | 20/20 | 20/30 | 20/30 | 20/20 |
| 5 | | | OS | J3 | J2 | J1 | J2 | 20/20 | 20/30 | 20/25 | 20/20 |
| 6 | F | 49 | OD | J5 | J1 | J1 | J3 | 20/25 | 20/30 | 20/30 | 20/25 |
| 6 | | | OS | J5 | J2 | J3 | J5 | 20/25 | 20/30 | 20/25 | 20/25 |
| 7 | M | 50 | OD | J3 | J1+ | J1+ | J1 | 20/30 | 20/40 | 20/40 | 20/40 |
| 7 | | | OS | J3 | J1+ | J1+ | J1 | 20/30 | 20/40 | 20/40 | 20/30 |
| 8 | F | 52 | OD | J5 | J2 | J2 | J3 | 20/20 | 20/25 | 20/25 | 20/20 |
| 8 | | | OS | J5 | J2 | J2 | J3 | 20/20 | 20/25 | 20/25 | 20/20 |
| 9 | M | 54 | OD | J10 | J3 | J3 | J5 | 20/25 | 20/20 | 20/20 | 20/20 |
| 9 | | | OS | J10 | J3 | J3 | J5 | 20/25 | 20/20 | 20/25 | 20/25 |
| 10 | F | 56 | OD | J16 | J5 | J5 | J7 | 20/30 | 20/30 | 20/30 | 20/25 |
| 10 | | | OS | J10 | J5 | J5 | J7 | 20/30 | 20/30 | 20/30 | 20/30 |

| ID | | Pre Sph | 1 h Sph | 4 h Sph | 6 h Sph | Pre Cyl | 1 h Cyl | 4 h Cyl | 6 h Cyl |
|---|---|---|---|---|---|---|---|---|---|
| 1 | OD | 1.00 | −0.25 | 0.00 | 0.50 | −0.25 | −0.50 | −0.50 | −0.25 |
| 1 | OS | 1.00 | −0.50 | −0.50 | −0.25 | −0.25 | −0.25 | −0.25 | −0.25 |
| 2 | OD | 0.00 | −0.75 | −0.50 | 0.00 | −0.25 | −0.50 | −0.25 | −0.25 |
| 2 | OS | 0.00 | −0.50 | −0.25 | 0.00 | −0.75 | −1.00 | −0.75 | −0.75 |
| 3 | OD | 0.00 | −0.25 | −0.50 | −0.25 | −0.25 | −0.25 | −0.50 | −0.25 |
| 3 | OS | 0.25 | −0.25 | 0.00 | 0.25 | −0.50 | −0.50 | −0.50 | −0.25 |
| 4 | OD | 0.75 | 0.00 | 0.25 | 0.50 | −0.50 | −0.50 | −0.25 | −0.50 |
| 4 | OS | 0.75 | 0.00 | 0.00 | 0.25 | −0.25 | −0.25 | −0.25 | −0.25 |
| 5 | OD | 0.25 | −0.50 | −0.50 | 0.00 | −0.25 | −0.50 | −0.25 | −0.25 |
| 5 | OS | 0.50 | 0.00 | −0.25 | 0.00 | 0.00 | −0.25 | −0.25 | 0.00 |
| 6 | OD | 0.25 | −0.25 | −0.25 | 0.00 | −0.75 | −0.50 | −0.50 | −0.50 |
| 6 | OS | 0.50 | −0.25 | 0.00 | 0.25 | −0.50 | −0.50 | −0.50 | −0.50 |
| 7 | OD | −0.25 | −0.50 | −0.50 | −0.25 | −0.50 | −0.50 | −0.75 | −0.75 |
| 7 | OS | 0.00 | −0.50 | −0.25 | −0.25 | −0.75 | −0.75 | −0.75 | −0.75 |
| 8 | OD | 0.25 | −0.25 | −0.25 | 0.00 | −0.25 | −0.25 | −0.25 | −0.25 |
| 8 | OS | 0.25 | −0.25 | −0.25 | 0.00 | 0.00 | −0.25 | −0.25 | 0.00 |
| 9 | OD | 0.75 | 0.00 | 0.25 | 0.50 | −0.25 | −0.25 | −0.25 | −0.25 |
| 9 | OS | 0.75 | 0.00 | 0.25 | 0.50 | −0.50 | −0.25 | −0.50 | −0.50 |
| 10 | OD | 0.75 | −0.25 | −0.25 | 0.00 | −0.25 | −0.25 | 0.00 | −0.25 |
| 10 | OS | 0.50 | 0.00 | 0.00 | 0.00 | −0.50 | −0.75 | −0.75 | −0.50 |
| AVERAGE | | 0.41 | −0.26 | −0.18 | 0.09 | −0.38 | −0.44 | −0.41 | −0.36 |

| ID | | Pre Sph Eq | 1 h Sph Eq | 4 h Sph Eq | 6 h Sph Eq | Pre Pupil | 1 h Pupil | 4 h Pupil | 6 h Pupil |
|---|---|---|---|---|---|---|---|---|---|
| 1 | OD | 0.88 | −0.50 | −0.25 | 0.38 | 5.1 | 1.9 | 2.2 | 3.1 |
| 1 | OS | 0.88 | −0.63 | −0.63 | −0.38 | 5.4 | 2 | 2.3 | 3.2 |
| 2 | OD | −0.13 | −1.00 | −0.63 | −0.13 | 5.2 | 2.2 | 2.2 | 3.6 |
| 2 | OS | −0.38 | −1.00 | −0.63 | −0.38 | 5.3 | 2.1 | 2.3 | 3.5 |
| 3 | OD | −0.13 | −0.38 | −0.75 | −0.38 | 5.1 | 2.3 | 2.5 | 3.2 |
| 3 | OS | 0.00 | −0.50 | −0.25 | 0.13 | 5.2 | 2.4 | 2.5 | 3.3 |
| 4 | OD | 0.50 | −0.25 | 0.13 | 0.25 | 6.1 | 2.3 | 2.6 | 3.9 |
| 4 | OS | 0.63 | −0.13 | −0.13 | 0.13 | 6 | 2.2 | 2.7 | 3.8 |
| 5 | OD | 0.13 | −0.75 | −0.63 | −0.13 | 5.4 | 2 | 2.1 | 3 |
| 5 | OS | 0.50 | −0.13 | −0.38 | 0.00 | 5.5 | 2 | 2.1 | 3 |
| 6 | OD | −0.13 | −0.50 | −0.50 | −0.25 | 4.7 | 2.3 | 2.2 | 3.1 |
| 6 | OS | 0.25 | −0.50 | −0.25 | 0.00 | 4.8 | 2.4 | 2.3 | 3 |
| 7 | OD | −0.50 | −0.75 | −0.88 | −0.63 | 4.3 | 2.2 | 2.4 | 3.3 |
| 7 | OS | −0.38 | −0.88 | −0.63 | −0.63 | 4.4 | 2 | 2.3 | 3.2 |
| 8 | OD | 0.13 | −0.38 | −0.38 | −0.13 | 4.6 | 2.1 | 2.2 | 3.7 |
| 8 | OS | 0.25 | −0.38 | −0.38 | 0.00 | 4.5 | 2 | 2.1 | 3.6 |
| 9 | OD | 0.63 | −0.13 | 0.13 | 0.38 | 4.2 | 2.2 | 2.4 | 3.2 |
| 9 | OS | 0.50 | −0.13 | 0.00 | 0.25 | 4.3 | 2.1 | 2.3 | 3.3 |
| 10 | OD | 0.63 | −0.38 | −0.25 | −0.13 | 4.1 | 1.9 | 2 | 2.9 |
| 10 | OS | 0.25 | −0.38 | −0.38 | −0.25 | 4.1 | 2 | 2 | 2.8 |
| AVERAGE | | 0.23 | −0.48 | −0.38 | −0.09 | 4.92 | 2.13 | 2.29 | 3.29 |

The observed improvement in the near vision is believed to have occurred for at least two reasons. First, an increase in the refractive power of the eye of roughly +0.70 diopters was observed following treatment that could compensate presbyopia and mild degrees of hyperopia. Second, the depth of visual field of the eye was increased by 0.50 to 0.75 diopters following treatment (probably related to the decrease in papillary diameter to about 2.0 mm) This observed increase in depth of field is believed to have:

1) potentiated the observed increase in refractive power of the eye to improve near vision in emmetropes, myopes and hyperopes
2) potentiated the observed increase in refractive power of the eye to improve distance visual acuity in mild hyperopes; and ;

3) compensated any loss in distance vision in emmetropic or myopic patients caused by the observed change in refractive, power of the eye.

Example 2

Five patients (ten eyes) from 30 to 55 years-old with "mild hyperopia" (i.e., eyes having a spherical equivalent from +0.50 to +2.00 D) were treated with three drops of 1% pilocarpine and 0.125% oxymetazoline separated 5 minutes. Following treatment, all of the patients were able to improve their unaided distance visual acuity at one and four hours. Thirty-five percent had an improvement in one line of distance vision at 6 hours Example 3

A group of 10 patients (20 eyes) considered emmetropes or slightly hyperopic (Spherical equivalent from +0.88 D to −0.13 D with less than 1.00 D of astigmatism) was treated with a composition of the invention. Each patient had an extensive ocular examination prior to treatment that included 1) refractive power of each eye; 2) the unaided distance visual acuity (UDVA) measured using Snellen chart; 3) the unaided near vision (UNVA) measured at 40 centimeters using a hand-held Rosembaum chart and the Jaeger notation; and 4) the pupillary diameter measured in medium lighting (mesopic) conditions with a special infra-red camera device.

Figure 3:
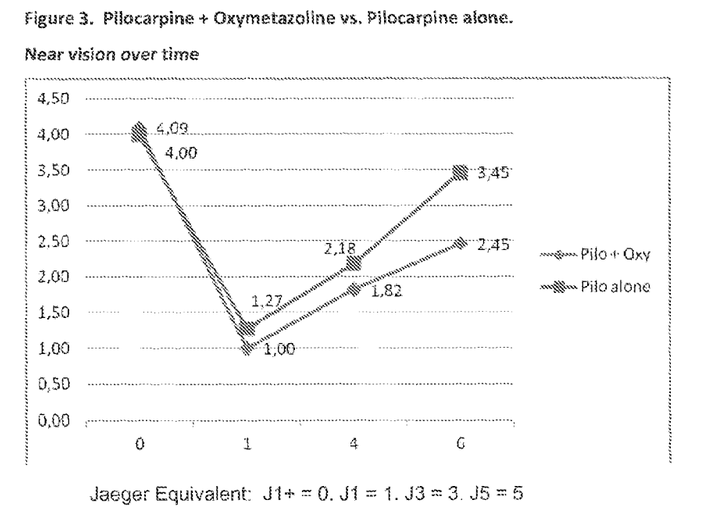
FIG. 3 shows a comparison of the effect of a composition comprising pilocarpine and oxymetazoline and a composition comprising pilocarpine alone on near vision (Jaeger Equivalent) over time.
Figure 4:
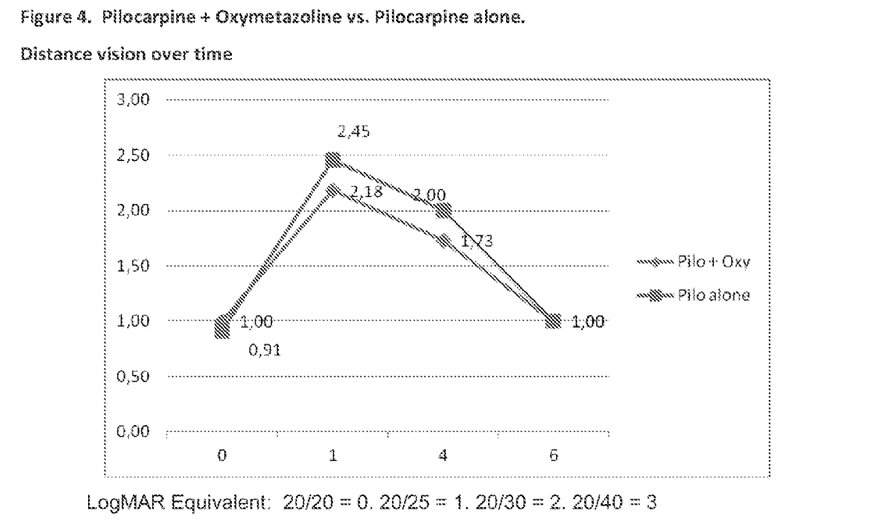
FIG. 4 shows a comparison of the effect of a composition comprising pilocarpine and oxymetazoline and a composition comprising pilocarpine alone on distance vision (LogMAR Equivalent) over time.

One drop containing 1% pilocarpine and 0.025% oxymetazoline w/w dissolved in a solution of 0.5% sodium chloride, with carboxymethyl cellulose as a viscosant and benzalkonitun chloride as preservative were instilled once into the right eye, and the same solution containing 1% pilocarpine without oxymetazoline was instilled once into the left eye and the same measurements were taken one hour, four hours and six hours later. (Each patient acted as its own control) (Table 2). As shown in Table 2 and FIGS. 3 and 4, it could be seen that when using pilocarpine alone the improvement in near vision was smaller and tended to wear out earlier, also there was more decrease in distance vision at the 1 and 4 hour time points. From the refractive standpoint, pilocarpine alone seemed to induce more astigmatism. This result was likely due to crystalline lens changes, whereas when pilocarpine was administered with oxymetazoline less astigmatism was induced. The addition of oxymetazoline improved pilocarpine's effect over the pupillary contraction thereby enhancing optical performance. Some discrepancy was noted in both groups between the obtained refractions and the unaided distance and near acuities, which may indicate that other factors are involved with the improvement in vision, for example increased high order optical measurements (aberrations) such as spherical aberration, coma, trefoil, etc.

TABLE 2

[Pilocarpine + Oxymetazoline(OD) vs. Pilocarpine alone (OS)]

| ID | Sex | Age | | Pre UNVA | 1 h UNVA | 4 h UNVA | 6 h UNVA | Pre UDVA | 1 h UDVA | 4 h UDVA | 6 h UDVA |
|---|---|---|---|---|---|---|---|---|---|---|---|
| 1 | M | 43 | OD | J1 | J1+ | J1 | J1 | 20/25 | 20/30 | 20/20 | 20/25 |
| 1 | | | OS | J1 | J1+ | J1 | J1 | 20/30 | 20/40 | 20/50 | 20/30 |
| 2 | F | 45 | OD | J2 | J1+ | J1 | J1 | 20/30 | 20/40 | 20/30 | 20/30 |
| 2 | | | OS | J3 | J1 | J3 | J3 | 20/30 | 20/50 | 20/40 | 20/30 |
| 3 | M | 45 | OD | J3 | J1+ | J1 | J2 | 20/20 | 20/30 | 20/40 | 20/20 |
| 3 | | | OS | J3 | J1+ | J1 | J2 | 20/20 | 20/30 | 20/20 | 20/20 |
| 4 | M | 46 | OD | J5 | J1+ | J2 | J3 | 20/20 | 20/30 | 20/30 | 20/25 |
| 4 | | | OS | J3 | J1 | J1 | J3 | 20/20 | 20/40 | 20/20 | 20/20 |
| 5 | M | 48 | OD | J3 | J1+ | J1 | J1 | 20/25 | 20/40 | 20/30 | 20/25 |
| 5 | | | OS | J5 | J1+ | J1 | J2 | 20/25 | 20/30 | 20/30 | 20/25 |
| 6 | F | 48 | OD | J7 | J1 | J2 | J3 | 20/40 | 20/30 | 20/25 | 20/30 |
| 6 | | | OS | J7 | J2 | J3 | J7 | 20/30 | 20/30 | 20/30 | 20/30 |
| 7 | M | 50 | OD | J5 | J2 | J3 | J5 | 20/25 | 20/30 | 20/25 | 20/25 |
| 7 | | | OS | J5 | J1 | J3 | J5 | 20/25 | 20/40 | 20/30 | 20/25 |
| 8 | M | 51 | OD | J5 | J2 | J3 | J3 | 20/20 | 20/40 | 20/40 | 20/20 |
| 8 | | | OS | J5 | J3 | J3 | J5 | 20/20 | 20/30 | 20/20 | 20/20 |
| 9 | F | 52 | OD | J7 | J3 | J3 | J5 | 20/30 | 20/40 | 20/40 | 20/30 |
| 9 | | | OS | J5 | J3 | J3 | J5 | 20/30 | 20/50 | 20/40 | 20/30 |
| 10 | F | 54 | OD | J7 | J3 | J3 | J3 | 20/25 | 20/30 | 20/30 | 20/25 |
| 10 | | | OS | J7 | J3 | J5 | J5 | 20/20 | 20/30 | 20/25 | 20/25 |

| ID | | Pre Sph | 1 h Sph | 4 h Sph | 6 h Sph | Pre Cyl | 1 h Cyl | 4 h Cyl | 6 h Cyl |
|---|---|---|---|---|---|---|---|---|---|
| 1 | OD | 1.00 | −0.25 | 0.00 | 0.50 | −0.25 | −0.50 | −0.50 | −0.25 |
| 1 | OS | 1.00 | −0.50 | −0.25 | 0.00 | −0.25 | −0.75 | −0.25 | −0.25 |
| 2 | OD | 0.00 | −0.75 | −0.50 | 0.00 | −0.25 | −0.50 | −0.25 | −0.25 |
| 2 | OS | 0.00 | −0.50 | −0.25 | 0.00 | −0.75 | −1.00 | −0.75 | −0.75 |
| 3 | OD | 0.00 | −0.25 | −0.50 | −0.25 | −0.25 | −0.25 | −0.50 | −0.25 |
| 3 | OS | 0.25 | 0.00 | 0.00 | 0.25 | −0.50 | −0.50 | −0.50 | −0.25 |
| 4 | OD | 0.75 | −0.50 | −0.25 | −0.25 | −0.50 | −0.50 | −0.25 | −0.50 |
| 4 | OS | 0.75 | −0.25 | −0.25 | 0.00 | −0.25 | −0.75 | −0.50 | −0.25 |
| 5 | OD | 0.25 | −0.50 | −0.50 | 0.00 | −0.25 | −0.50 | −0.25 | −0.25 |
| 5 | OS | 0.50 | 0.00 | −0.25 | 0.25 | 0.00 | −0.25 | −0.25 | 0.00 |
| 6 | OD | 0.25 | −0.25 | −0.25 | 0.00 | −0.75 | −0.50 | −0.50 | −0.50 |
| 6 | OS | 0.50 | 0.00 | 0.00 | 0.25 | −0.50 | −0.50 | −0.50 | −0.50 |
| 7 | OD | 0.25 | −0.25 | −0.50 | 0.25 | −0.50 | −0.50 | −0.75 | −0.75 |
| 7 | OS | 0.00 | −0.50 | −0.25 | −0.25 | −0.75 | −0.75 | −0.75 | −0.75 |
| 8 | OD | 0.25 | −0.25 | −0.25 | 0.00 | −0.25 | −0.25 | −0.25 | −0.25 |
| 8 | OS | 0.25 | −0.25 | −0.25 | 0.00 | 0.00 | −0.25 | −0.25 | 0.00 |
| 9 | OD | 0.75 | 0.00 | 0.25 | 0.50 | −0.25 | −0.25 | −0.25 | −0.25 |
| 9 | OS | 0.75 | 0.25 | 0.50 | 0.50 | −0.50 | −0.25 | −0.50 | −0.50 |
| 10 | OD | 0.75 | −0.25 | −0.25 | 0.00 | −0.25 | −0.25 | 0.00 | −0.25 |

TABLE 2-continued

| | | | | | [Pilocarpine + Oxymetazoline(OD) vs. Pilocarpine alone (OS)] | | | |
|---|---|---|---|---|---|---|---|---|
| 10 | OS | 0.50 | 0.00 | 0.25 | 0.50 | −0.50 | −0.75 | −0.75 | −0.50 |
| | | | | | AVERAGE | | | |
| Pilo + Oxy | | 0.61 | −0.48 | −0.25 | 0.43 | −0.39 | −0.41 | −0.39 | −0.36 |
| Pilo + NACl | | 0.59 | −0.32 | −0.14 | 0.57 | −0.36 | −0.59 | −0.59 | −0.43 |

| ID | | Pre Sph Eq | 1 h Sph Eq | 4 h Sph Eq | 6 h Sph Eq | Pre Pupil | 1 h Pupil | 4 h Pupil | 6 h Pupil |
|---|---|---|---|---|---|---|---|---|---|
| 1 | OD | 1.00 | −0.50 | −0.13 | 0.25 | 5.5 | 2 | 2.5 | 4.7 |
| 1 | OS | 0.63 | −1.00 | −0.88 | 0.25 | 5.6 | 2.1 | 2.7 | 4.9 |
| 2 | OD | 0.50 | −1.13 | −0.75 | 0.38 | 5.2 | 2.2 | 2.6 | 4.8 |
| 2 | OS | 0.13 | −1.00 | −0.75 | 0.38 | 5.3 | 2.3 | 2.8 | 4.9 |
| 3 | OD | 0.38 | −0.75 | −0.75 | 0.13 | 4.8 | 2.1 | 2.5 | 4.7 |
| 3 | OS | 0.50 | −0.25 | −0.13 | 0.38 | 4.7 | 2.2 | 2.5 | 4.7 |
| 4 | OD | 0.50 | −1.00 | −0.63 | 0.25 | 4.9 | 2.3 | 2.7 | 4.5 |
| 4 | OS | 0.63 | −0.88 | −0.63 | 0.63 | 4.8 | 2.3 | 2.9 | 4.4 |
| 5 | OD | 0.50 | −1.00 | −0.75 | 0.25 | 4.1 | 2.1 | 2.7 | 4 |
| 5 | OS | 0.63 | −0.63 | −0.50 | 0.50 | 4 | 2.2 | 2.8 | 4.2 |
| 6 | OD | 0.88 | −0.63 | −0.25 | 0.63 | 4.7 | 1.9 | 2.2 | 4.8 |
| 6 | OS | 0.75 | −0.50 | −0.38 | 0.50 | 4.7 | 2.1 | 2.4 | 4.9 |
| 7 | OD | 0.50 | −0.50 | −0.13 | 0.38 | 4.3 | 2.3 | 2.5 | 3.9 |
| 7 | OS | 0.38 | −0.75 | −0.50 | 0.38 | 4.2 | 2.4 | 3 | 4.1 |
| 8 | OD | 0.13 | −0.88 | −0.50 | 0.25 | 4.1 | 2.2 | 2.4 | 4 |
| 8 | OS | 0.13 | −0.50 | −0.50 | 0.13 | 4.2 | 2.4 | 2.9 | 4.2 |
| 9 | OD | 0.38 | −0.63 | −0.50 | 0.38 | 4.5 | 2.5 | 2.6 | 4.4 |
| 9 | OS | 0.50 | −0.75 | −0.38 | 0.25 | 4.4 | 2.5 | 2.6 | 4.4 |
| 10 | OD | −0.13 | −0.50 | −0.50 | −0.13 | 4.7 | 2.1 | 2.9 | 4.7 |
| 10 | OS | 0.25 | −0.50 | −0.13 | 0.50 | 4.8 | 2.1 | 3.1 | 4.7 |
| | | | | | AVERAGE | | | | |
| Pilo + Oxy | | 0.42 | −0.68 | −0.44 | 0.25 | 4.25 | 1.93 | 2.33 | 4.05 |
| Pilo + NaCl | | 0.41 | −0.61 | −0.43 | 0.35 | 4.25 | 2.05 | 2.52 | 4.13 |

Example 4

A larger number of patients (n=65) from 40 to 56 years-old with refractions front +0.50 D to −0.25 D (spherical equivalent) with less than −1.00 D of astigmatism were given eye drops to use three times a day. The eye drops contained 1% pilocarpine and 0.0125% oxymetazoline. The patients were seen one week after the start of treatment and then monthly to refill the drop prescription for six months. Only four patients discontinued use of the eye drops due to hick of effect (one patient) or side effects such as brow ache or ocular pain (three patients). The rest of the patients continued using the medication to improve their near vision in lieu of reading glasses. No significant side effects were reported from this cohort of real life patients. Minor side effects including a sense of decreased illumination (likely associated with the pupillary constriction) and ocular floaters (the pinhole effect improves vision not only for the objects outside the eye but also for the minor irregularities floating inside the eye) were reported by patients in several instances.

In another group of patients with higher degrees of myopia, hyperopia or astigmatism, the eye drops were used over their contact lenses or distance glasses to avoid using bifocal glasses.

The refractive improvement was very similar to example 1, where there was an increase in the refractive power of the eye of about 0.50 diopters on the average without affecting the cylindrical (astigmatic) component. In the patients with higher degrees of myopia, hyperopia or astigmatism, there was usually a 2 to 4 line gain in near visual acuity with the distance visual acuity either improving one line, remaining unchanged or dropping one to two lines according to the baseline refraction. The effect lasted over time and patients noticed that as they used the drops on a regular basis, there was a cumulative effect where the effect of the drops seemed to last longer. Also, these patients noted a decrease in any mild irritation/redness that the drops might have caused initially. Two-thirds of the patients were using the herein mentioned drops exclusively and the other third used them most of the time but also used reading glasses occasionally (at night at home, etc.) in lieu of the drops.

Example 5

After a two-week washout period, five of the patients from example 1 were treated with a combination of 1% pilocarpine and 0.015% meloxicam dissolved in a solution of 0.5% sodium chloride in water plus carboxymethyl cellulose as viscosant and benzalkoaium chloride as a preservative, and the same measurements in example 1 were taken at one hour, four hours, and eight hours later.

TABLE 3

| | | | | | | (Pilocarpine + Meloxicam) | | | | | |
|---|---|---|---|---|---|---|---|---|---|---|---|
| ID | Sex | Age | | | Pre UNVA | 1 h UNVA | 4 h UNVA | 6 h UNVA | Pre UDVA | 1 h UDVA | 4 h UDVA | 6 h UDVA |
| 1 | M | 43 | OD | | J2 | J1 | J1 | J2 | 20/20 | 20/20 | 20/20 | 20/20 |
| 1 | | | OS | | J1 | J1+ | J1+ | J1 | 20/20 | 20/20 | 20/20 | 20/20 |

TABLE 3-continued (Pilocarpine + Meloxicam)

| | | | | | | | | | | | |
|---|---|---|---|---|---|---|---|---|---|---|---|
| 2 | M | 46 | OD | J2 | J1 | J2 | J2 | 20/25 | 20/40 | 20/40 | 20/30 |
| 2 | | | OS | J3 | J2 | J2 | J2 | 20/25 | 20/30 | 20/25 | 20/25 |
| 3 | F | 49 | OD | J5 | J2 | J2 | J3 | 20/25 | 20/40 | 20/40 | 20/30 |
| 3 | | | OS | J7 | J2 | J5 | J5 | 20/25 | 20/40 | 20/30 | 20/40 |
| 4 | F | 52 | OD | J7 | J5 | J5 | J5 | 20/30 | 20/25 | 20/25 | 20/20 |
| 4 | | | OS | J5 | J3 | J3 | J5 | 20/30 | 20/20 | 20/25 | 20/25 |
| 5 | F | 55 | OD | J10 | J5 | J7 | J7 | 20/25 | 20/40 | 20/30 | 20/30 |
| 5 | | | OS | J10 | J5 | J5 | J7 | 20/25 | 20/30 | 20/40 | 20/25 |

| ID | | Pre Sph | 1 h Sph | 4 h Sph | 6 h Sph | Pre Cyl | 1 h Cyl | 4 h Cyl | 6 h Cyl |
|---|---|---|---|---|---|---|---|---|---|
| 1 | OD | 0.75 | 0.25 | 0.50 | 0.50 | −0.25 | −0.50 | −0.50 | −0.25 |
| 1 | OS | 0.75 | 0.25 | 0.25 | 0.25 | −0.50 | −0.50 | −0.50 | −0.50 |
| 2 | OD | −0.25 | −0.75 | −0.50 | −0.50 | −0.25 | −0.50 | −0.25 | −0.25 |
| 2 | OS | −0.25 | −0.50 | −0.25 | −0.25 | 0.00 | 0.00 | −0.25 | −0.25 |
| 3 | OD | 0.25 | −0.50 | −0.50 | −0.25 | −0.75 | −0.50 | −0.50 | −0.50 |
| 3 | OS | 0.25 | −0.50 | −0.25 | −0.25 | −0.50 | −0.25 | −0.25 | −0.50 |
| 4 | OD | 0.75 | 0.00 | 0.25 | 0.00 | 0.00 | −0.25 | −0.25 | −0.25 |
| 4 | OS | 0.75 | 0.25 | 0.25 | 0.25 | −0.50 | −0.25 | −0.50 | −0.50 |
| 5 | OD | 0.25 | −0.50 | −0.25 | 0.00 | −0.75 | −0.50 | −0.50 | −0.75 |
| 5 | OS | 0.25 | −0.25 | −0.25 | 0.00 | −0.50 | −0.50 | −0.75 | −0.50 |
| AVERAGE | | 0.35 | −0.23 | −0.08 | −0.03 | −0.38 | −0.38 | −0.43 | −0.43 |

| ID | | Pre Sph Eq | 1 h Sph Eq | 4 h Sph Eq | 6 h Sph Eq | Pre Pupil | 1 h Pupil | 4 h Pupil | 6 h Pupil |
|---|---|---|---|---|---|---|---|---|---|
| 1 | OD | 0.63 | 0.00 | 0.25 | 0.38 | 5.3 | 2.1 | 2.2 | 3.2 |
| 1 | OS | 0.50 | 0.00 | 0.00 | 0.00 | 5.4 | 2.2 | 2.3 | 3.4 |
| 2 | OD | −0.38 | −1.00 | −0.63 | −0.63 | 5.8 | 2.3 | 2.6 | 3.9 |
| 2 | OS | −0.25 | −0.50 | −0.63 | −0.38 | 5.6 | 2.2 | 2.7 | 3.7 |
| 3 | OD | −0.13 | −0.75 | −0.75 | −0.50 | 4.9 | 2.4 | 2.6 | 3.2 |
| 3 | OS | 0.00 | −0.63 | −0.38 | −0.50 | 4.7 | 2.3 | 2.4 | 3.2 |
| 4 | OD | 0.75 | −0.13 | 0.13 | −0.13 | 4.5 | 2.2 | 2.2 | 3.8 |
| 4 | OS | 0.50 | 0.13 | 0.00 | 0.00 | 4.5 | 2 | 2.1 | 3.8 |
| 5 | OD | −0.13 | −0.75 | −0.50 | −0.38 | 4 | 2.2 | 2.4 | 3 |
| 5 | OS | 0.00 | −0.50 | −0.63 | −0.25 | 4.1 | 2.1 | 2.2 | 3.1 |
| AVERAGE | | 0.15 | −0.41 | −0.31 | −0.24 | 4.88 | 2.2 | 2.37 | 3.43 |

Figure 5:
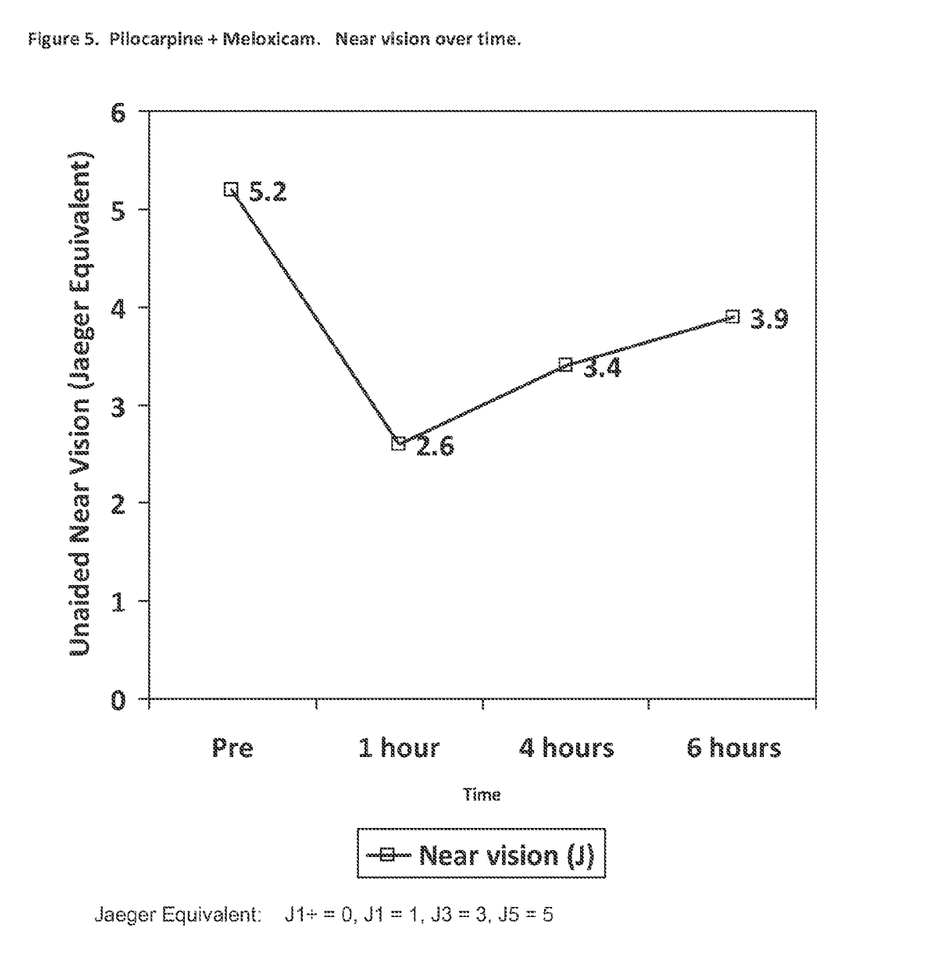
FIG. 5 shows the effect of a composition comprising pilocarpine and meloxicam on near vision (Jaeger Equivalent) over time.
Figure 6:
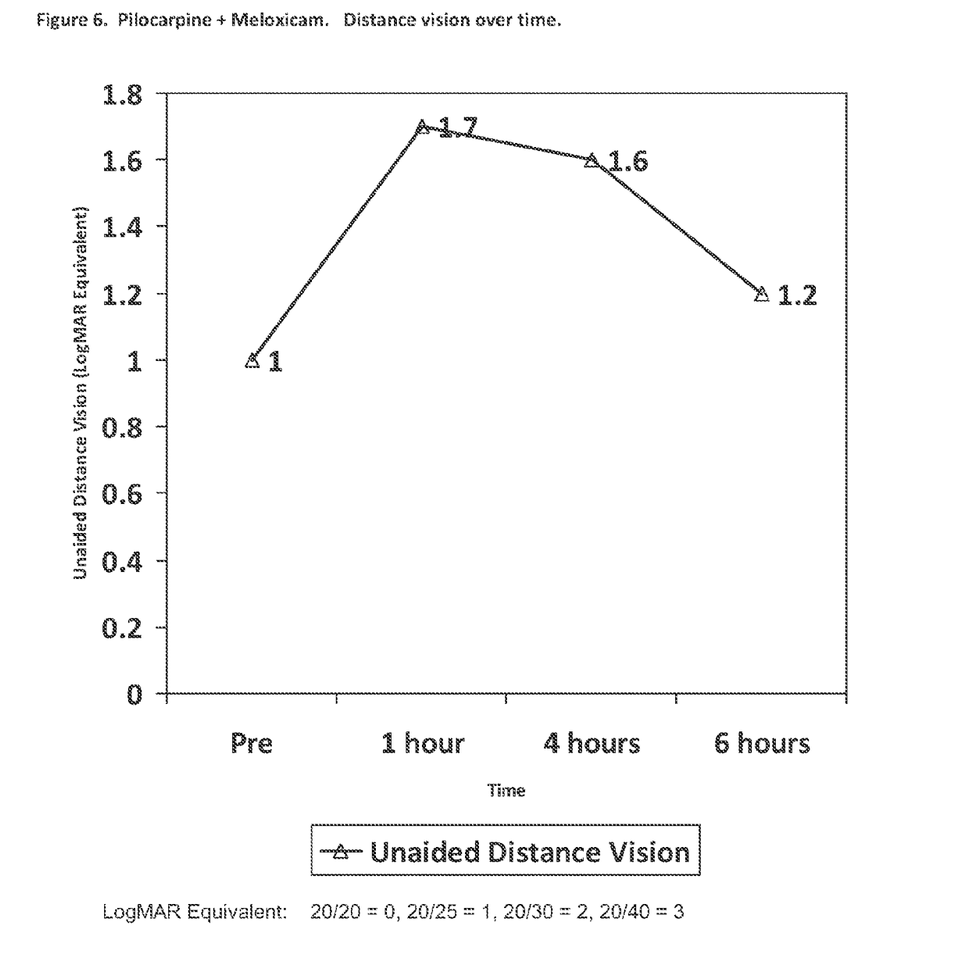
FIG. 6 shows the effect of a composition comprising pilocarpine and meloxicam on distance vision (LogMAR Equivalent) over time.

As shown in Table 3 and FIG. 5, when using the combination of pilocarpine and meloxicam there was a myopization of around 0.57 diopters and an improvement in unaided near acuity of 2.6 lines at one hour which is less than that obtained by the pharmacological combination presented in example 1 but still of good clinical usage. The drop in distance visual acuity was 0.6 lines at one our (FIG. 6). Overall the pilocarpine/meloxicam results could be interpreted as the latter having a mitigating effect on the side effects of pilocarpine since it is not known to affect any of the receptors involved in near vision. This is in contrast with the preparation in example 1 where there seems to be a synergistic effect between the two described compounds.

Example 6

After a two-week washout period, the patients from example $ were treated with a combination of 1% pilocarpine and 0.1% naphazoline dissolved in a solution of 0.5% sodium chloride in water plus carboxymethyl cellulose as viscosant and benzalkonium chloride as preservative. Both eyes in the patients were treated and the same measurements as in example 5 were taken at one hour, four hours, and eight hours later. After another two week washout period, the patients were treated with a combination of 1% pilocarpine and 0.05% tetrahyrpzoline dissolved in a solution of 0.5% sodium chloride in water plus earboxymethyl cellulose as viscosant and benzalkonium chloride as preservative. Both eyes in the patients were treated and the same measurements as in example 5 were taken at one hour, four hours, and eight hours later. In both treatment groups, an improvement in near vision with a very modest decrease in unaided distance vision was observed. These results are similar to the observed results in example 5 and demonstrate a mitigation of the side effects of pilocarpine by naphazoline and tetrahydrozoline with modest potentiation of the therapeutic effects of pilocarpine.

While certain embodiments of the invention have been described, other embodiments may exist. While the specification includes a detailed description, the invention's scope is indicated by the following claims. Furthermore, while the specification has been described in language specific to structural features and/or methodological acts, the claims are not limited to the features or acts described above. Rather, the specific features and acts described above are disclosed as illustrative aspects and embodiments of the invention. Various other aspects, embodiments, modifications, and equivalents thereof which, after reading the description herein, may suggest themselves to one of ordinary skill in the art without departing from the spirit of the present invention or the scope of the claimed subject matter.

What is claimed is:

1. A composition for treatment of an ocular condition comprising presbyopia, comprising
   a muscarinic acetylcholine receptor M$_3$ agonist comprising pilocarpine, and
   an alpha-stimulant agonist having an imidazoline group comprising oxymetazoline,
   wherein the composition is therapeutically effective in the treatment of the ocular condition for at least six hours.

2. The composition of claim 1, wherein the composition comprises:
   from about 0.01% to about 4% w/v pilocarpine; and
   from about 0.01% to about 0.5% w/v oxymetazoline.

3. The composition of claim 1, wherein the composition comprises:
   from about 0.01% to about 2% w/v pilocarpine; and
   from about 0.01% to about 0.2% w/v oxymetazoline.

4. The composition of claim 1, wherein the composition comprises:
   from about 0.5% to about 1.5% w/v pilocarpine; and
   from about 0.02% to about 0.1% w/v oxymetazoline.

5. The composition of claim 1, wherein the composition further comprises an ophthalmically acceptable carrier.

6. The composition of claim 1, wherein the composition further comprises a cyclodextrin or derivative thereof to enhance ocular penetration of the composition.

7. The composition of claim 1, wherein the composition is in the form of an eye drop, suspension, gel, ointment, injectable solution, or spray.

8. The composition of claim 1, wherein the composition comprises from about 0.01% to about 10% w/v pilocarpine and from about 0.01% to about 0.5% w/v oxymetazoline.

9. The composition of claim 1, wherein the composition comprises from about 0.5% to about 2% w/v pilocarpine and from about 0.02% to about 0.125% w/v oxymetazoline.

10. The composition of claim 1, wherein the composition comprises from about 0.03% to about 1.8% w/v pilocarpine.

11. The composition of claim 1, wherein the composition comprises from about 0.00625% to about 0.125% w/v oxymetazoline.

* * * * *